United States Patent
Wason

(10) Patent No.: US 10,803,425 B1
(45) Date of Patent: Oct. 13, 2020

(54) FACILITATING PATIENT APPOINTMENT SCHEDULING

(71) Applicant: ALLSCRIPTS SOFTWARE, LLC, Chicago, IL (US)

(72) Inventor: Skyler Livermore Wason, Durham, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 669 days.

(21) Appl. No.: 14/701,415

(22) Filed: Apr. 30, 2015

(51) Int. Cl.
  *G06Q 10/10* (2012.01)
  *G06Q 50/22* (2018.01)
  *G06F 3/0488* (2013.01)

(52) U.S. Cl.
  CPC ....... *G06Q 10/1095* (2013.01); *G06F 3/0488* (2013.01); *G06Q 50/22* (2013.01)

(58) Field of Classification Search
  None
  See application file for complete search history.

(56) References Cited

U.S. PATENT DOCUMENTS

| | | | | |
|---|---|---|---|---|
| 8,244,566 B1 * | 8/2012 | Coley | ............. | G06Q 10/109 705/7.11 |
| 2010/0185465 A1 * | 7/2010 | Rana | ............. | G06Q 10/107 705/3 |
| 2012/0066015 A1 * | 3/2012 | Loeffen | ............. | G06Q 10/02 705/5 |
| 2016/0253464 A1 * | 9/2016 | Balwani | ............. | G06Q 50/22 705/2 |

OTHER PUBLICATIONS

Larson et al., Transparent Mid-Tier Database Caching in SQL Server, Jun. 2003, https://citeseerx.ist.psu.edu/viewdoc/download;jsessionid=27CD171B86F84334408B93EBFE5CB5C2?doi=10.1.1.95.875&rep=rep1&type=pdf (Year: 2003).*

* cited by examiner

*Primary Examiner* — Devin C Hein
(74) *Attorney, Agent, or Firm* — Medley, Behrens & Lewis, LLC

(57) ABSTRACT

A method includes displaying to a patient, via a touchscreen display of a mobile device, a date selection interface which includes a calendar display of days in a month; receiving user input corresponding to selection of a first one or more days of the month; displaying an interface displaying available appointment times for the first one or more days of the month; receiving user input corresponding to an indication to continue searching for an available appointment time; and displaying, to the patient via the touchscreen display of the mobile device, an updated date selection interface which has been updated to indicate availability of the first one or more days of the month.

12 Claims, 21 Drawing Sheets

US 10,803,425 B1

FACILITATING PATIENT APPOINTMENT SCHEDULING

INCORPORATION BY REFERENCE

The present application hereby incorporates herein by reference the entire disclosure of Appendix A hereto.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The present invention generally relates to patient appointment scheduling. A need exists for improvement in patient appointment scheduling. This need and other needs are addressed by one or more aspects of the present invention.

SUMMARY OF THE INVENTION

The present invention includes many aspects and features. Moreover, while many aspects and features relate to, and are described in, the context of patient appointment scheduling utilizing a mobile device, the present invention is not limited to use only in this context, as will become apparent from the following summaries and detailed descriptions of aspects, features, and one or more embodiments of the present invention.

Accordingly, one aspect of the present invention relates to a method comprising displaying, to a patient via a touchscreen display of a mobile device, an interface of a mobile application which includes a list of one or more providers with whom the patient may schedule an appointment; receiving, at the mobile device via the touchscreen display of the mobile device, user input corresponding to selection of one of the providers; displaying, to the patient via the touchscreen display of the mobile device, a date selection interface which includes a calendar display of days in a month; receiving, at the mobile device via the touchscreen display of the mobile device, user input corresponding to selection of a first one or more days of the month; displaying, in response to the received input corresponding to selection of the first one or more days of the month, an interface displaying available appointment times for the first one or more days of the month; receiving, at the mobile device via the touchscreen display of the mobile device, user input corresponding to an indication to continue searching for an available appointment time; and displaying, to the patient via the touchscreen display of the mobile device, an updated date selection interface which has been updated to indicate availability of the first one or more days of the month.

In a feature of this aspect, the mobile device comprises a phone.

In a feature of this aspect, the mobile device comprises a tablet.

In a feature of this aspect, the mobile device comprises an iPhone.

In a feature of this aspect, the mobile device comprises an iPad.

In a feature of this aspect, the mobile device comprises an iOS device.

In a feature of this aspect, the mobile device comprises an Android phone.

In a feature of this aspect, the mobile device comprises an Android tablet.

In a feature of this aspect, the mobile device comprises an Android device.

In a feature of this aspect, the updated date selection interface comprises a calendar display in which one or more days are underlined to indicate that one or more appointment times are available on those one or more days.

In a feature of this aspect, the updated date selection interface comprises a calendar display in which one or more days are greyed out to indicate that an appointment time is not available on those one or more days.

Another aspect relates to a method comprising displaying, to a patient via a touchscreen display of a mobile device, an interface of a mobile application which includes a list of one or more providers with whom the patient may schedule an appointment; receiving, at the mobile device via the touchscreen display of the mobile device, user input corresponding to selection of one of the providers; displaying, to the patient via the touchscreen display of the mobile device, a date selection interface which includes a calendar display of days in a month; receiving, at the mobile device via the touchscreen display of the mobile device, user input corresponding to selection of a first one or more days of the month; displaying, in response to the received input corresponding to selection of the first one or more days of the month, an interface displaying available appointment times for the first one or more days of the month; receiving, at the mobile device via the touchscreen display of the mobile device, user input corresponding to an indication to continue searching for an available appointment time; and displaying, to the patient via the touchscreen display of the mobile device, an updated date selection interface which has been updated to indicate that there are available appointment times for the first one or more days of the month.

In a feature of this aspect, the updated date selection interface comprises a calendar display in which one or more days are underlined to indicate that one or more appointment times are available on those one or more days.

In a feature of this aspect, the mobile device comprises a phone.

In a feature of this aspect, the mobile device comprises a tablet.

In a feature of this aspect, the mobile device comprises an iOS device.

In a feature of this aspect, the mobile device comprises an Android device.

Another aspect, relates to a method comprising displaying, to a patient via a touchscreen display of a mobile device, an interface of a mobile application which includes a list of one or more providers with whom the patient may schedule an appointment; receiving, at the mobile device via the touchscreen display of the mobile device, user input corresponding to selection of one of the providers; displaying, to the patient via the touchscreen display of the mobile device, a date selection interface which includes a calendar display of days in a month; receiving, at the mobile device via the touchscreen display of the mobile device, user input corresponding to selection of a first one or more days of the month; displaying, in response to the received input corresponding to selection of the first one or more days of the month, an interface indicating that there are no available appointment times for the first one or more days of the month; receiving, at the mobile device via the touchscreen display of the mobile device, user input corresponding to an indication to continue searching for an available appointment time; displaying, to the patient via the touchscreen display of the mobile device, an updated date selection interface which has been updated to indicate that there is no availability for the first one or more days of the month.

In a feature of this aspect, the updated date selection interface comprises a calendar display in which the first one or more days are greyed out to indicate that an appointment time is not available on those one or more days.

In a feature of this aspect, the mobile device comprises a phone.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals, and wherein.

DETAILED DESCRIPTION

Figure 1:
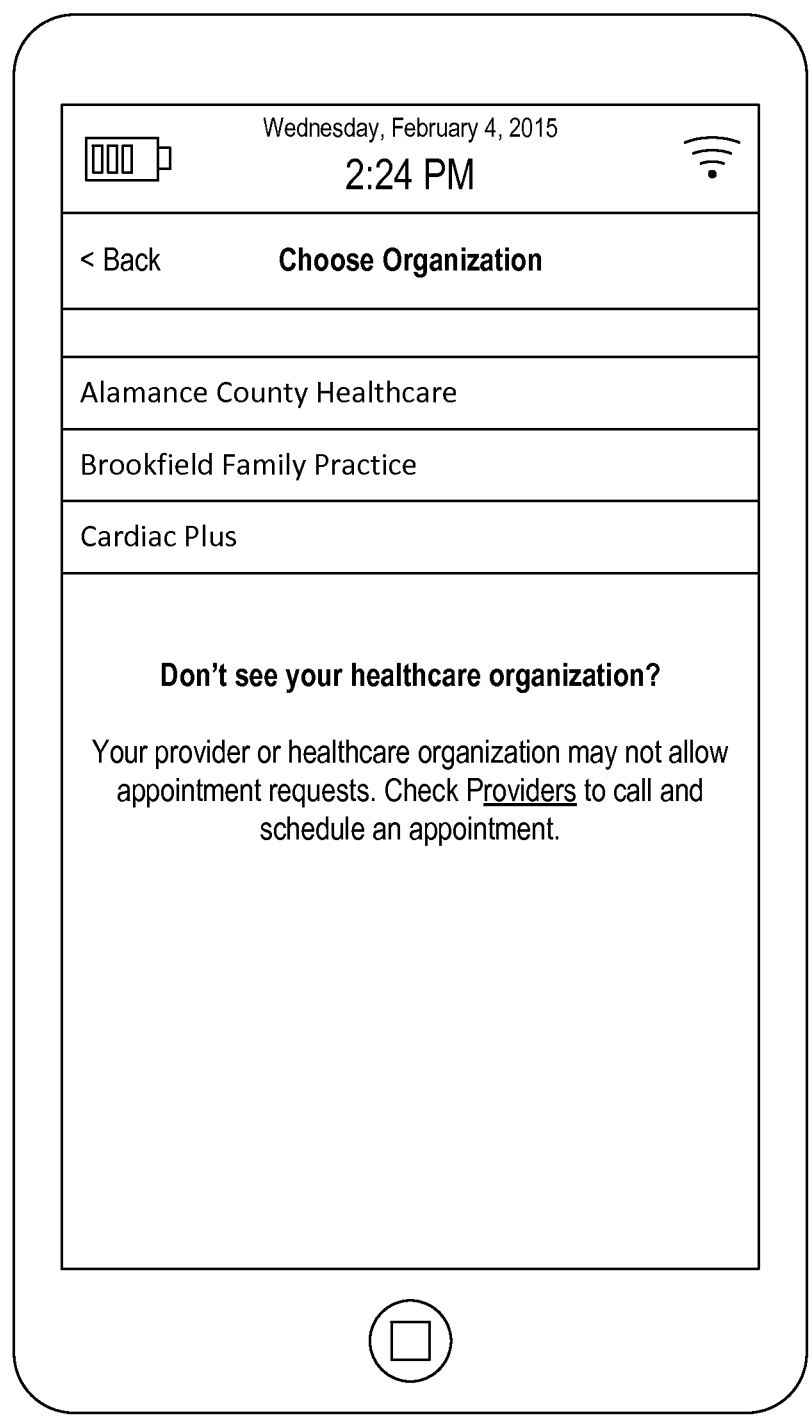
FIG. 1 illustrates an exemplary interface of a mobile application in accordance with one or more preferred implementations.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention in any claim of a patent issuing here from, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the issued claim(s) rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Regarding applicability of 35 U.S.C. 112, paragraph 6 or subsection (f), no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

In accordance with one or more preferred implementations, an application on a mobile device allows a patient to schedule an appointment with a medical provider. Preferably, the mobile application allows a patient to search for available appointments, and, upon identifying an available appointment date and time, request an appointment at that date and time.

In accordance with one or more preferred implementations, provider appointment data for one or more providers is managed in a practice management system. In one or more preferred implementations, an application on a mobile device queries such a practice management system to obtain appointment data for a provider. Preferably, a mobile application is configured to query multiple, distinct practice management systems which may each maintain appointment data for different providers.

FIG. 1 illustrates an exemplary interface of a mobile application in accordance with one or more preferred implementations. Preferably, the mobile application allows a patient user who is associated or connected with one or more health organizations to select an organization that they are associated with. FIG. 1 illustrates an interface for a patient user who is associated with three organizations. In accordance with one or more preferred implementations, a mobile application may allow patient users to look up organizations that they have not previously been associated or connected with.

Figure 2:
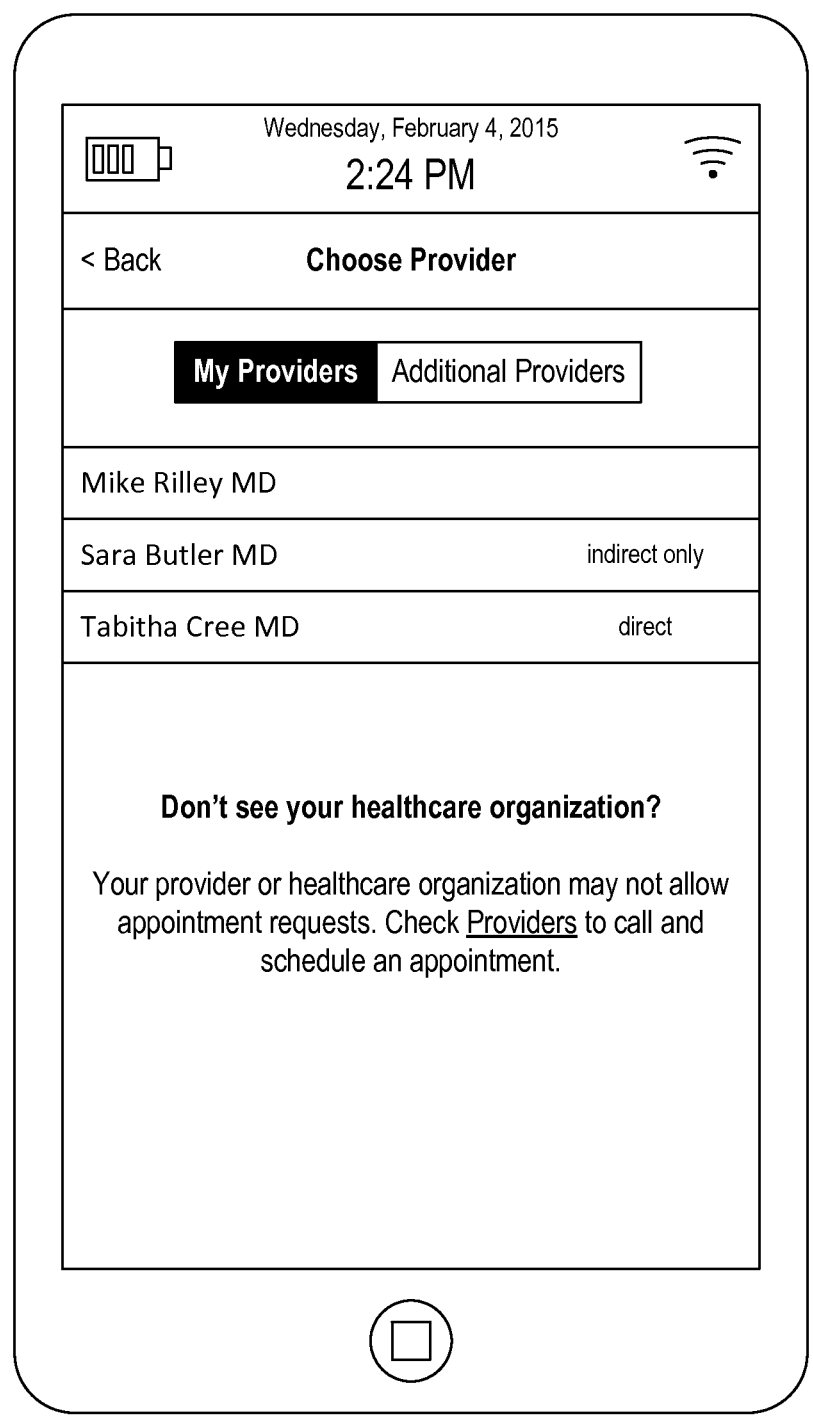
FIG. 2 illustrates an exemplary interface which presents a list of providers for an organization for selection by a patient user.

Preferably, once a patient user has selected an organization, they are presented with a list of healthcare providers to potentially schedule an appointment with. FIG. 2 illustrates an exemplary interface which presents a list of providers for that organization for selection by a patient user. Preferably, these providers include providers who are associated with the patient user, e.g. providers who have provided care in the past. In accordance with one or more preferred implementations, the interface may allow a patient user to view other providers for the organization as well.

In accordance with one or more preferred implementations, providers may be set up to support direct scheduling through the application, or may only be set up to support indirect scheduling. Preferably, this is indicated via an interface, as illustrated in FIG. 2.

Figure 3:
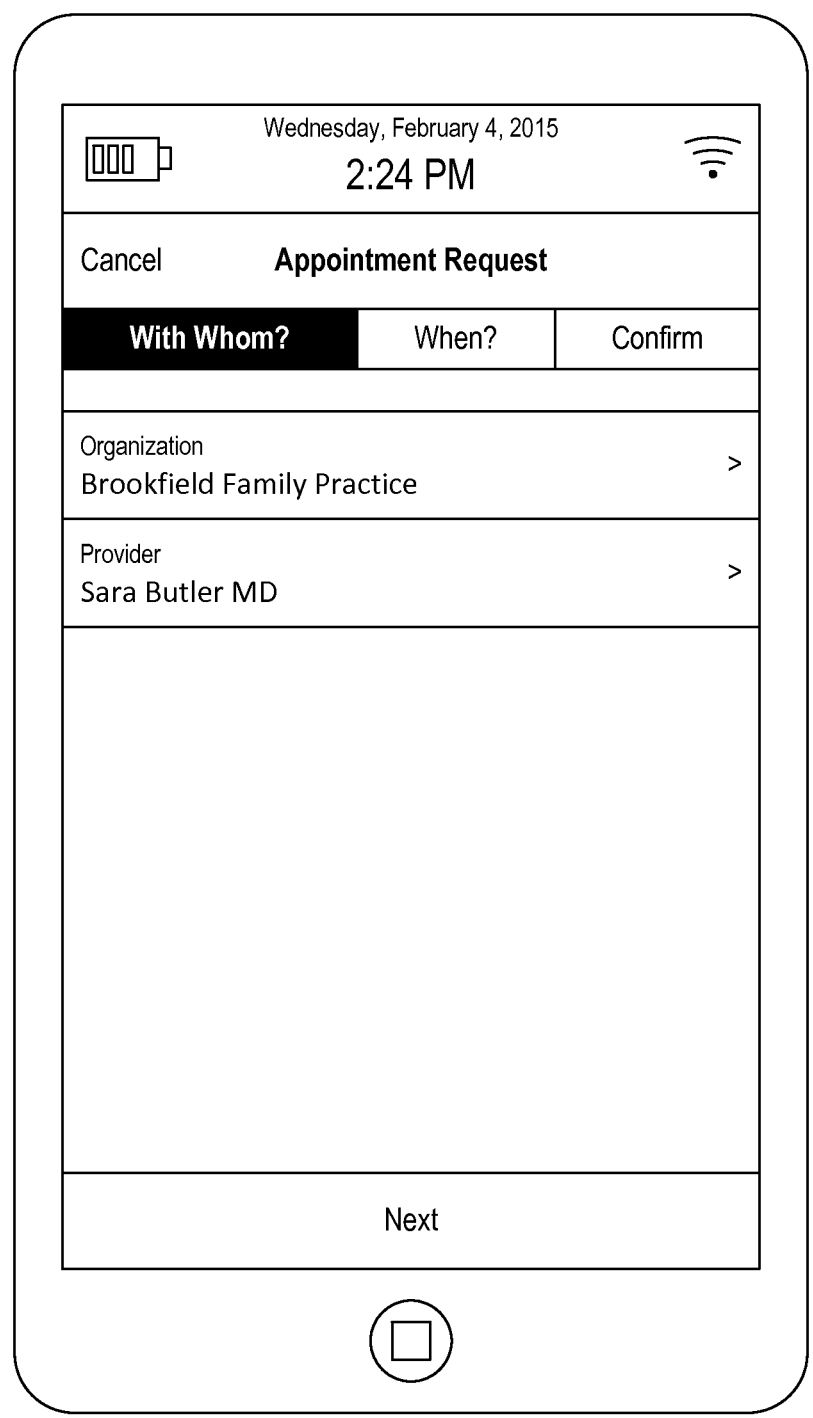
FIG. 3 illustrates an appointment request interface for an indirect appointment request.

FIG. 3 illustrates an appointment request interface for an indirect appointment request a patient user might be presented with upon selecting provider Sara Butler, who only supports indirect scheduling.

Figure 4:
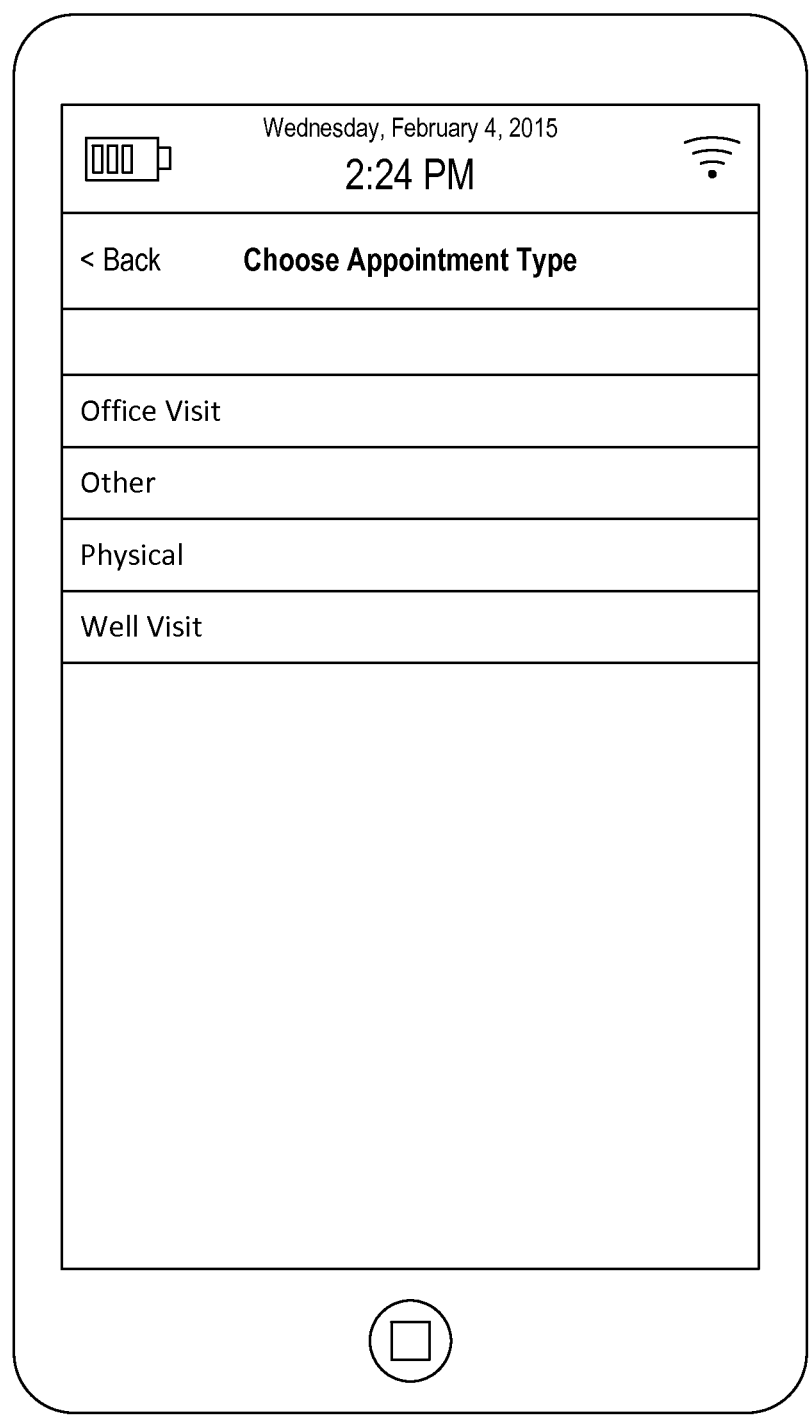
FIG. 4 illustrates an interface allowing a user to select an appointment type for an appointment request.

In contrast to this, in accordance with one or more preferred implementations, if a provider is set up for direct scheduling, a patient user may be able to select an appointment type for an appointment request, as illustrated in FIG. 4.

Figure 5:
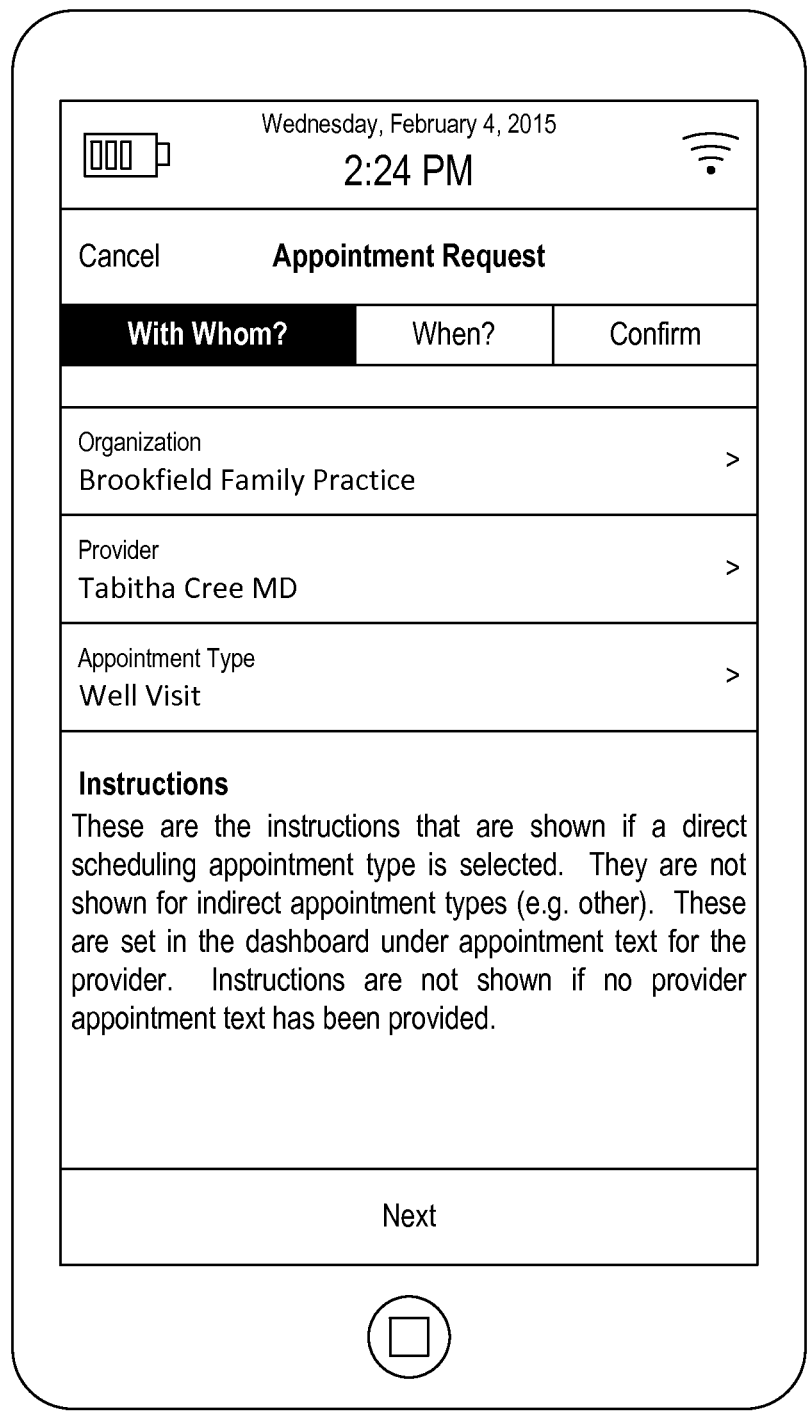
FIG. 5 illustrates an appointment request interface for a direct appointment request.

In accordance with one or more preferred implementations, providers set up to support direct scheduling are able to provide instructions to a patient user, as illustrated in FIG. 5, which illustrates an appointment request interface for a direct appointment request a patient user might be presented with upon selecting provider Tabitha Cree.

Figure 6:
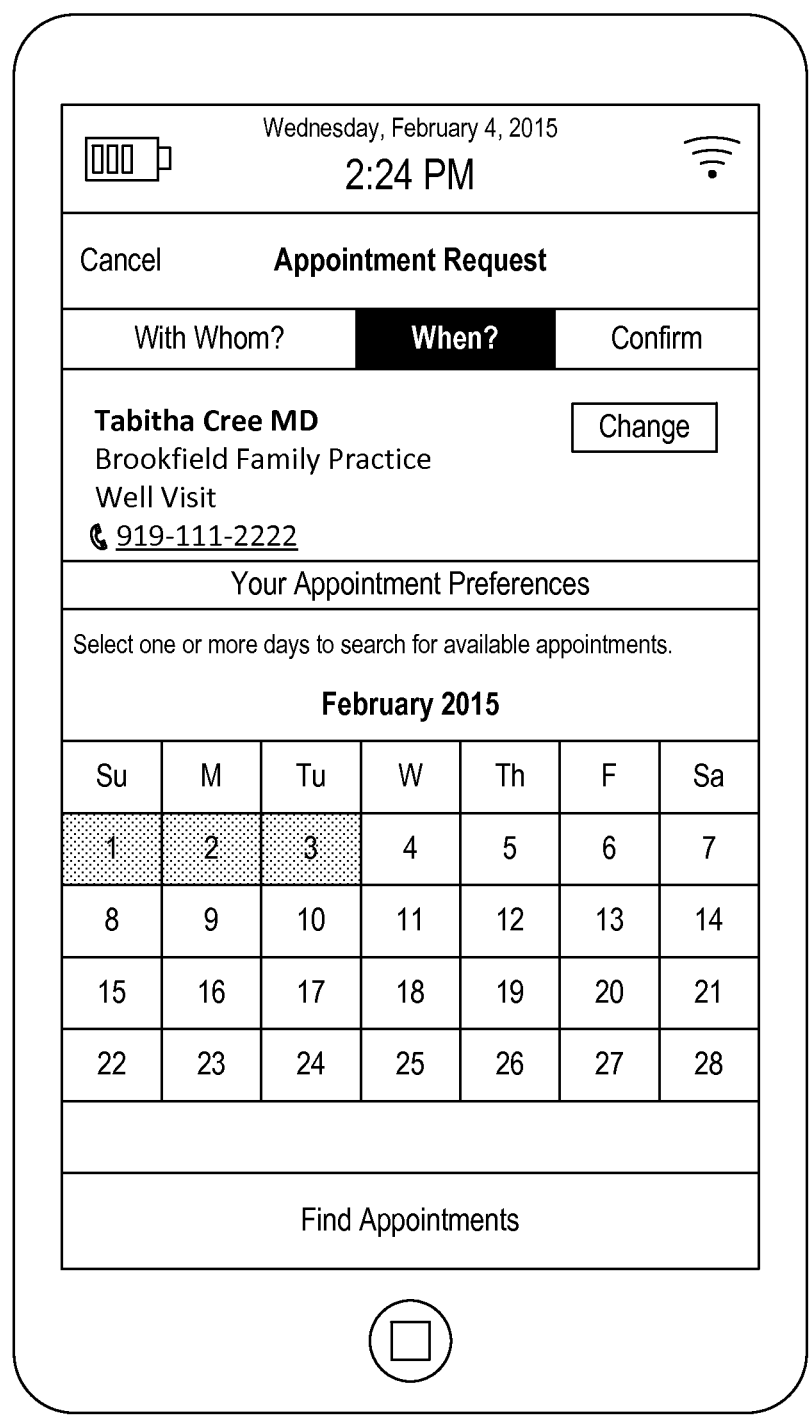
FIG. 6 illustrates an exemplary date selection interface which allows a patient user to indicate one or more days for which to search for an available appointment time.

Preferably, after a patient user has identified a provider he or she wishes to schedule an appointment with, he or she is presented with a date selection interface which allows the user to indicate one or more days for which to search for an available appointment time. FIG. 6 illustrates an exemplary date selection interface which allows a patient user to indicate one or more days for which to search for an available appointment time. Preferably, days in the past are indicated to be unavailable, such as by being grayed out, as illustrated in FIG. 6. In accordance with one or more preferred implementations, weekends may be indicated to be unavailable, although in at least some preferred implementations, weekends will not initially be indicated to be unavailable and can be searched just as other days can be. In accordance with one or more preferred implementations, a date selection interface may somehow indicate a reduced likelihood that weekend days will be available, e.g. by greying out Sunday and Saturday headers.

Figure 7:
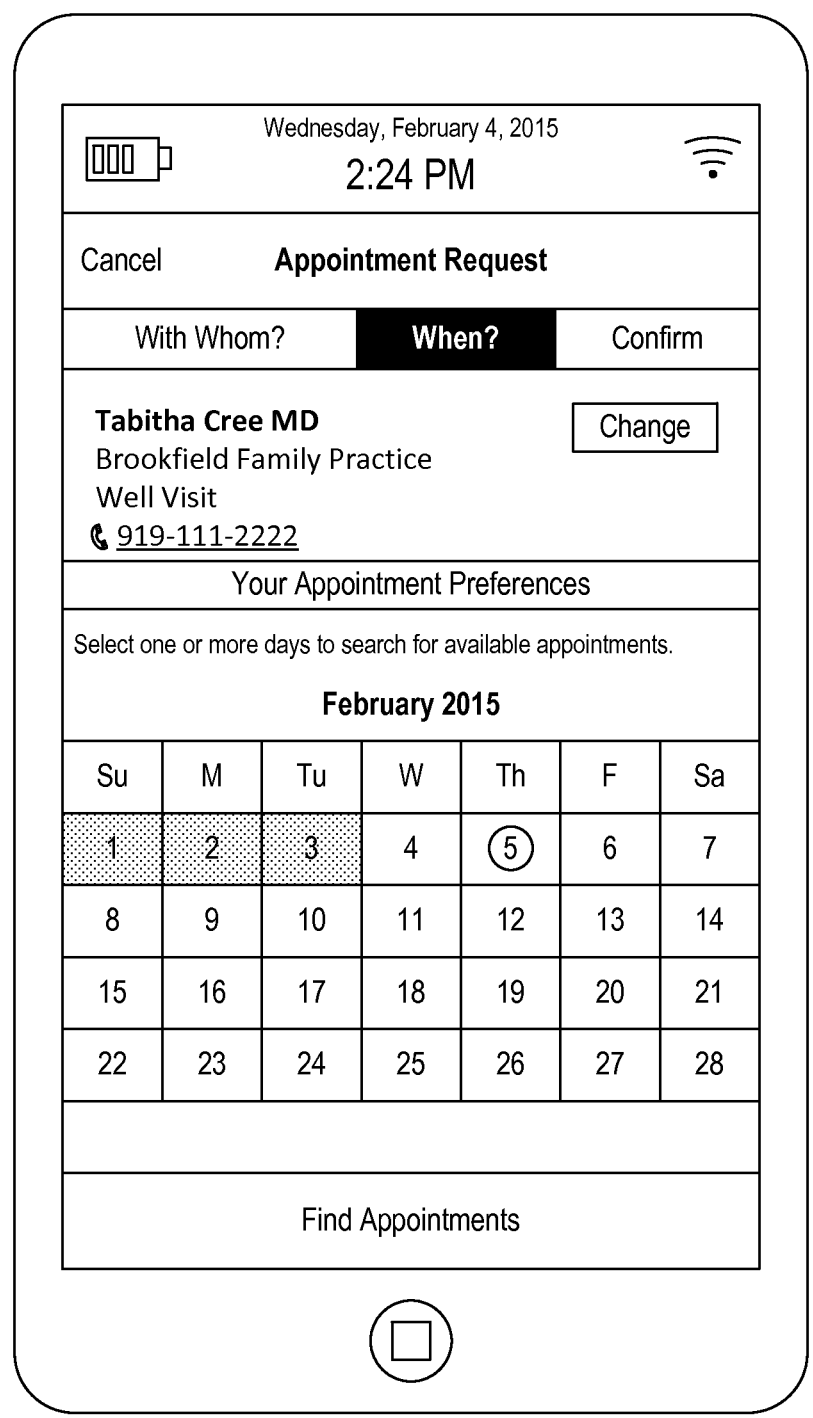
FIGS. 7-8 illustrate updating of a date selection interface.
Figure 8:
Figure 9:
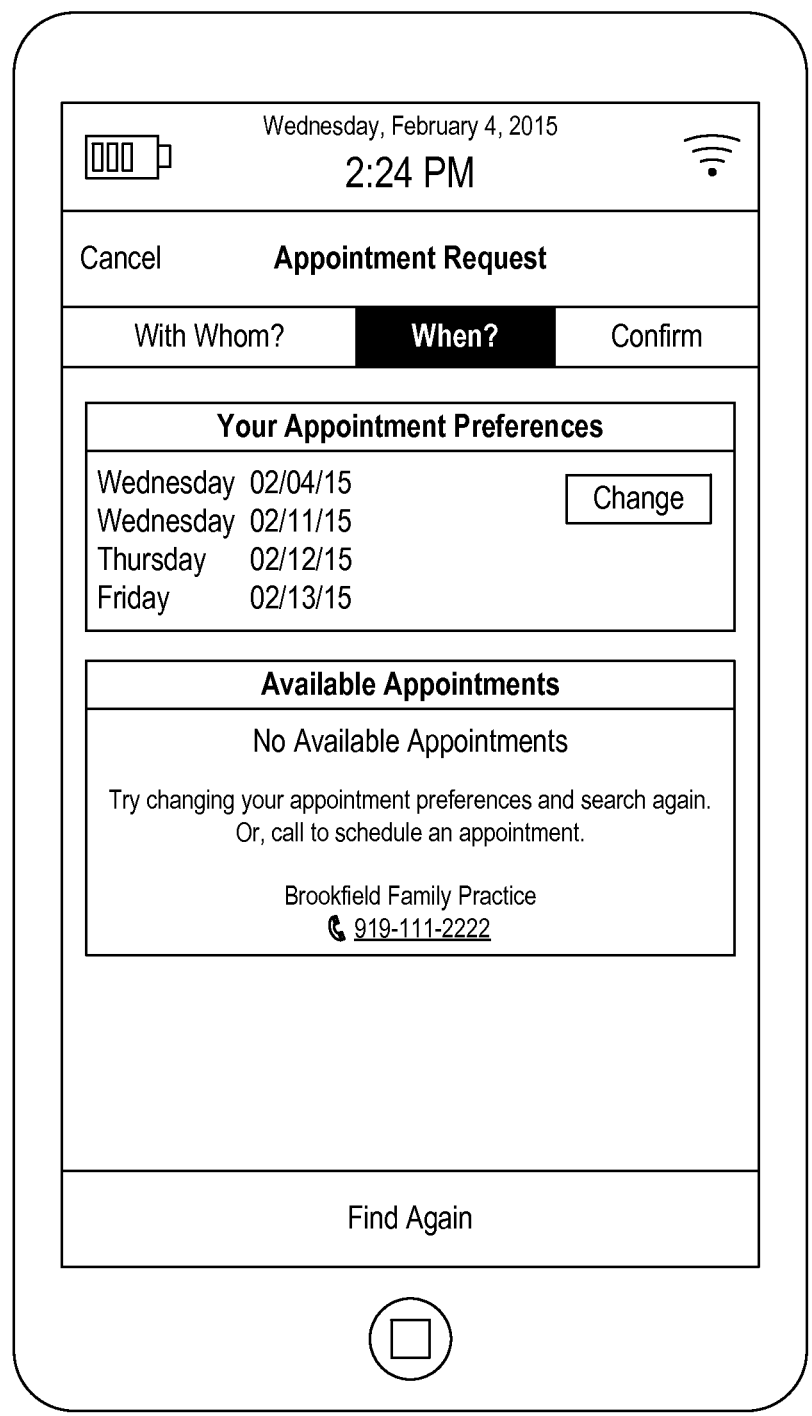
FIG. 9 illustrates an interface which indicates that there is no availability for days selected for searching.

In use, a patient user can select one or more days, e.g. by touching a portion of a touchscreen display on which is displayed an indication of that day. FIG. 7 illustrates updating of a date selection interface to illustrate that a user has selected Thursday, Feb. 5, 2015 as a day to search for available appointments, and FIG. 8 illustrates further updating to illustrate that a user has selected February 11, February 12, and February 13 as well. Upon selecting one or more days, a patient user can search for availability on those one or more days via a "Find Appointments" button. FIG. 9 illustrates an exemplary interface providing information on availability for selected days. The interface of FIG. 9 illustrates that there is no availability for the days selected for searching, and allows the user to search again.

Figure 10:
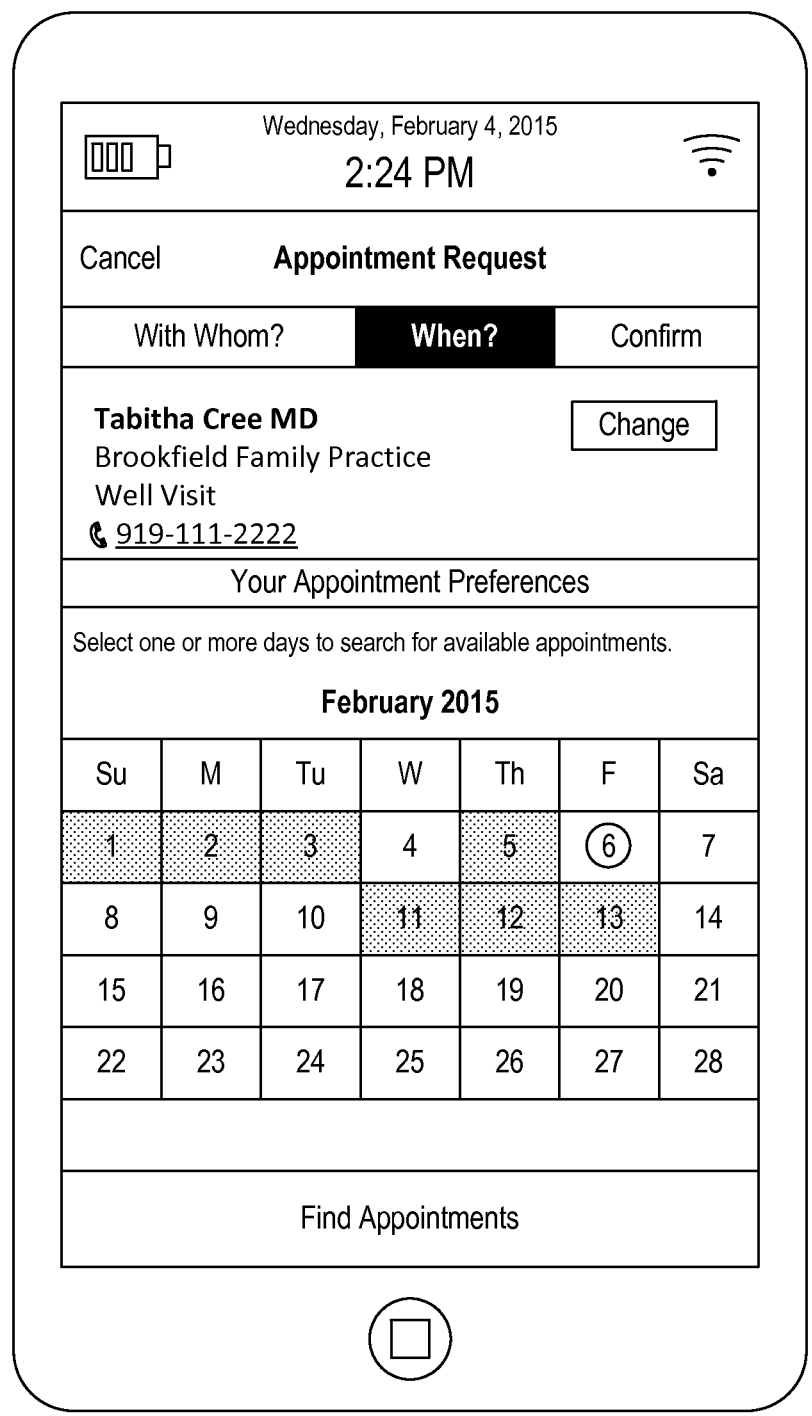
FIG. 10 illustrates an updated date selection interface in which days which have been determined to have no availability are indicated to have no availability.

Upon indicating that he or she wishes to search again, the user is presented with an updated date selection interface. The application preferably utilizes the information from the prior search, e.g. that there is no availability for certain days, to update the date selection interface in a manner which indicates such unavailability, e.g. by greying out those days. FIG. 10 illustrates such an updated date selection interface in which days which have been determined to have no availability are indicated to have no availability. Preferably, the application functions to continually update the date selection interface with additional information as additional searches are performed during the same session. In accordance with one or more preferred implementations, search information is cached or saved and may be utilized in later sessions as well, while in one or more preferred implementations, search information is only utilized in a current application or search session and not saved or cached for later use beyond such application or search session.

Upon being presented with an updated date selection interface, a user may once again select one or more days to search for available appointment times, as illustrated in FIG. 10.

Figure 11:
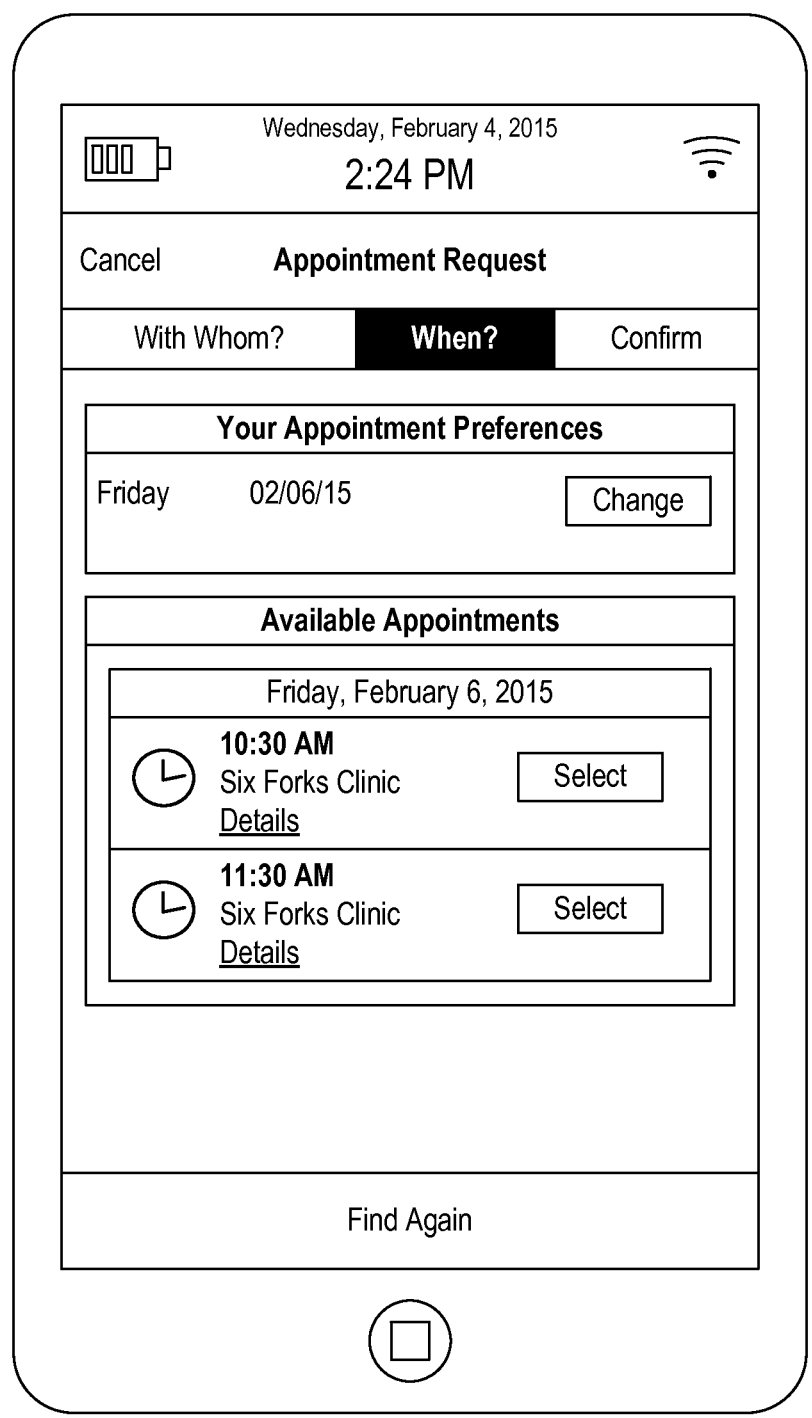
FIG. 11 illustrates an exemplary interface indicating availability for a selected day.

FIG. 11 illustrates an exemplary interface indicating availability for a selected day, namely Friday Feb. 6, 2015.

The interface allows a user to select one of the available appointment times, view additional details for the available appointment times, or go back and try to find another available appointment time.

Figure 12:
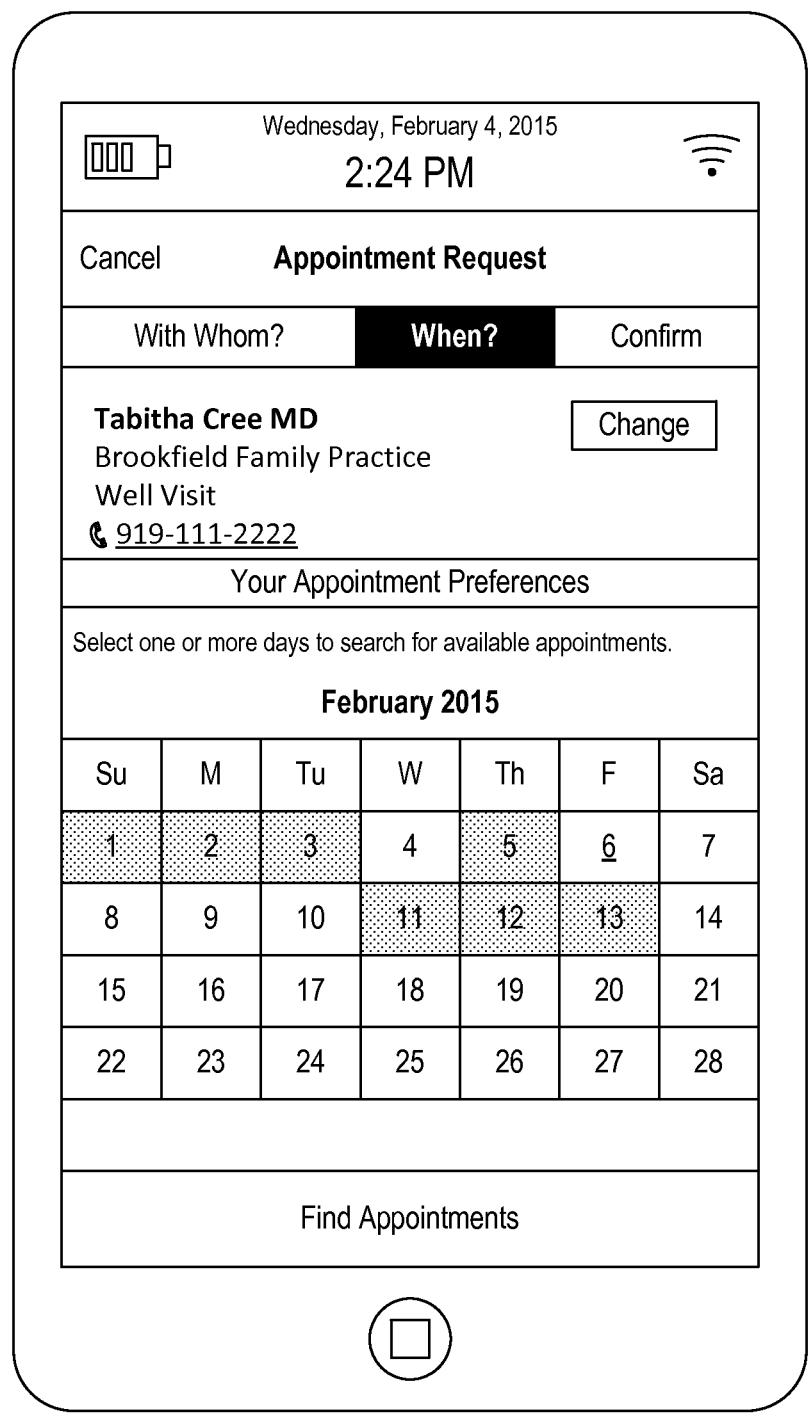
FIG. 12 illustrates an updated date selection interface.

Preferably, if a user chooses to try to find another available appointment time, the user will be returned to an updated date selection interface. The application preferably utilizes the information from the prior search to update the date selection interface to reflect that there are appointment times available on February 6, e.g. by underlining that day on the interface, as illustrated in FIG. 12.

Figure 13:
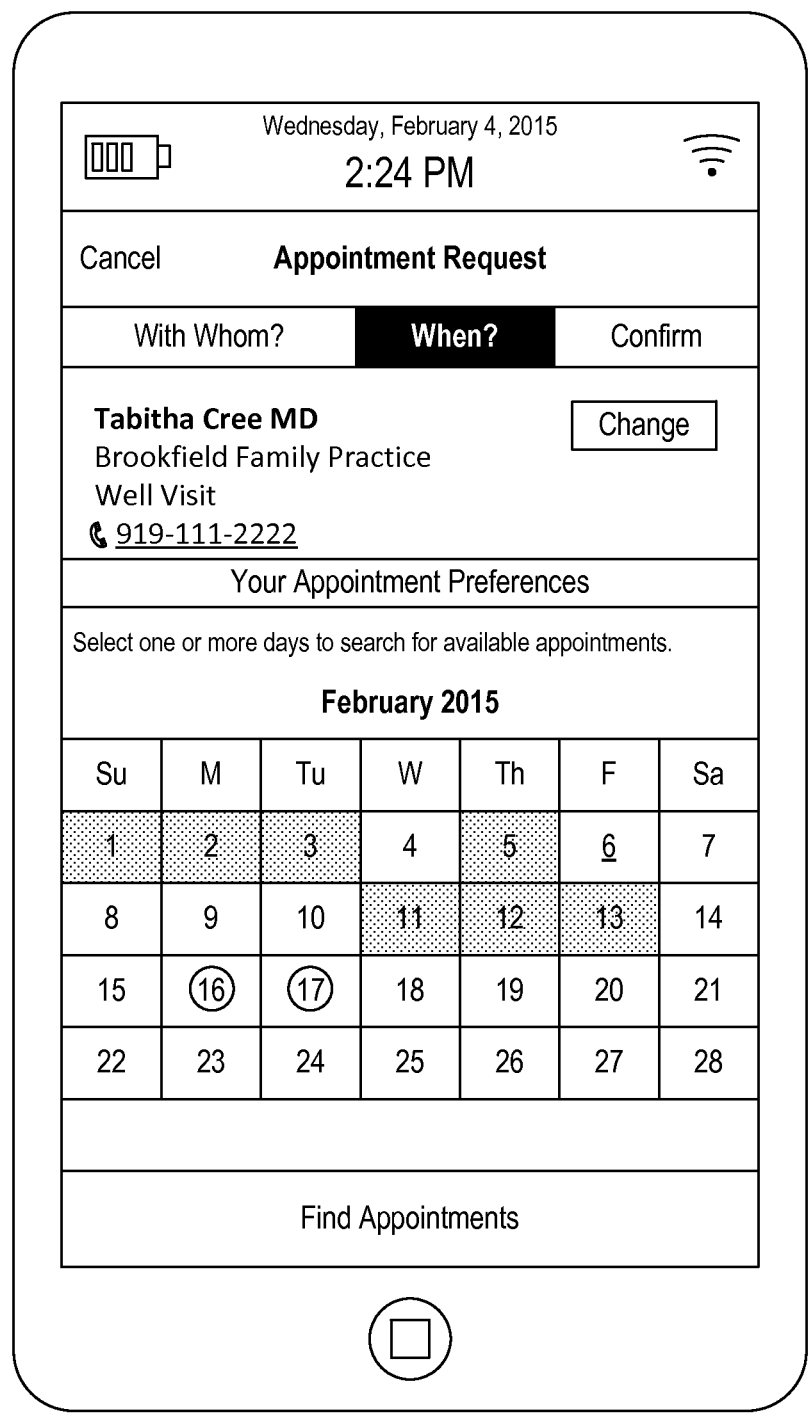
FIG. 13 illustrates selection of one or more dates.

Upon being presented with such an updated date selection interface, a user may once again select one or more days to search for available appointment times, as illustrated in FIG. 13.

Figure 14:
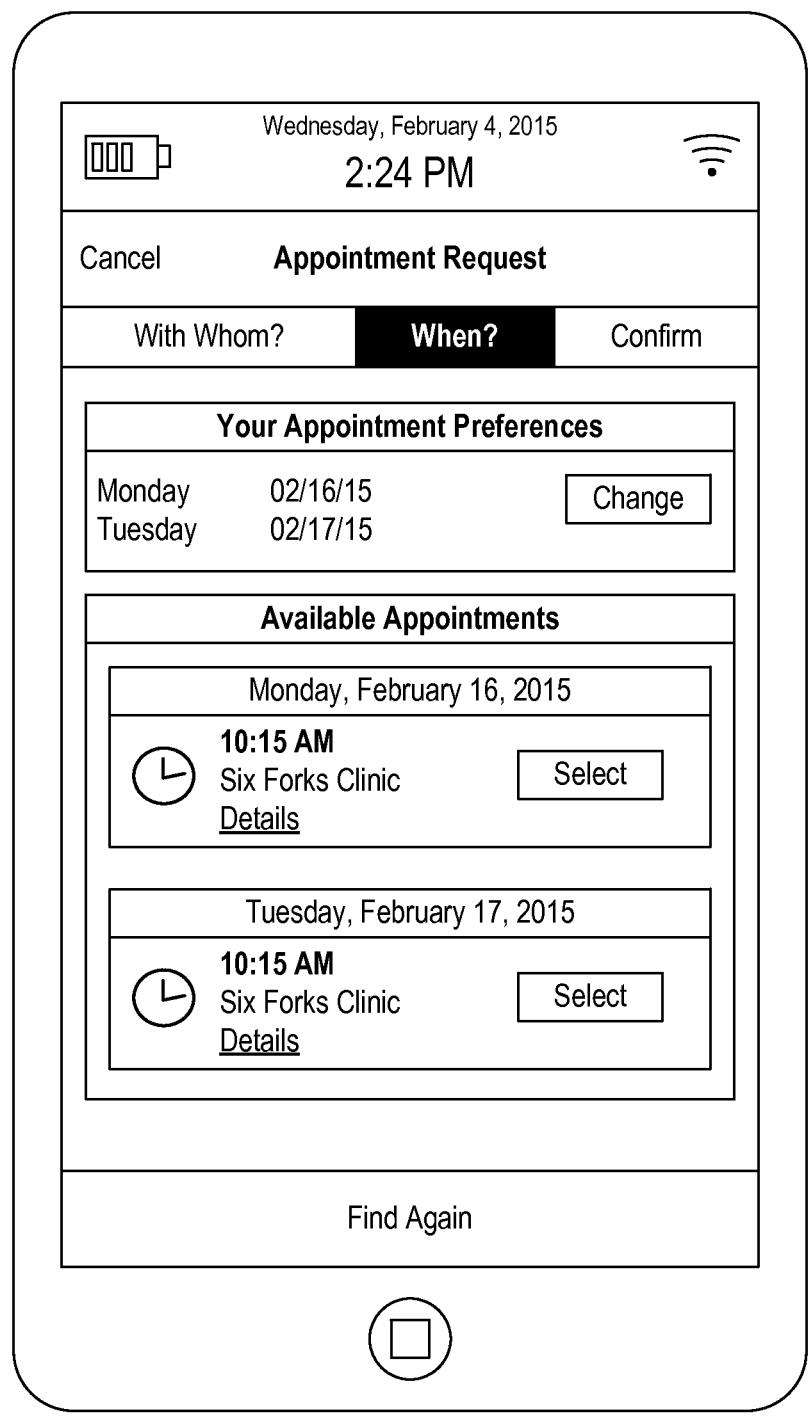
FIG. 14 illustrates an exemplary interface indicating availability for selected days.
Figure 15:
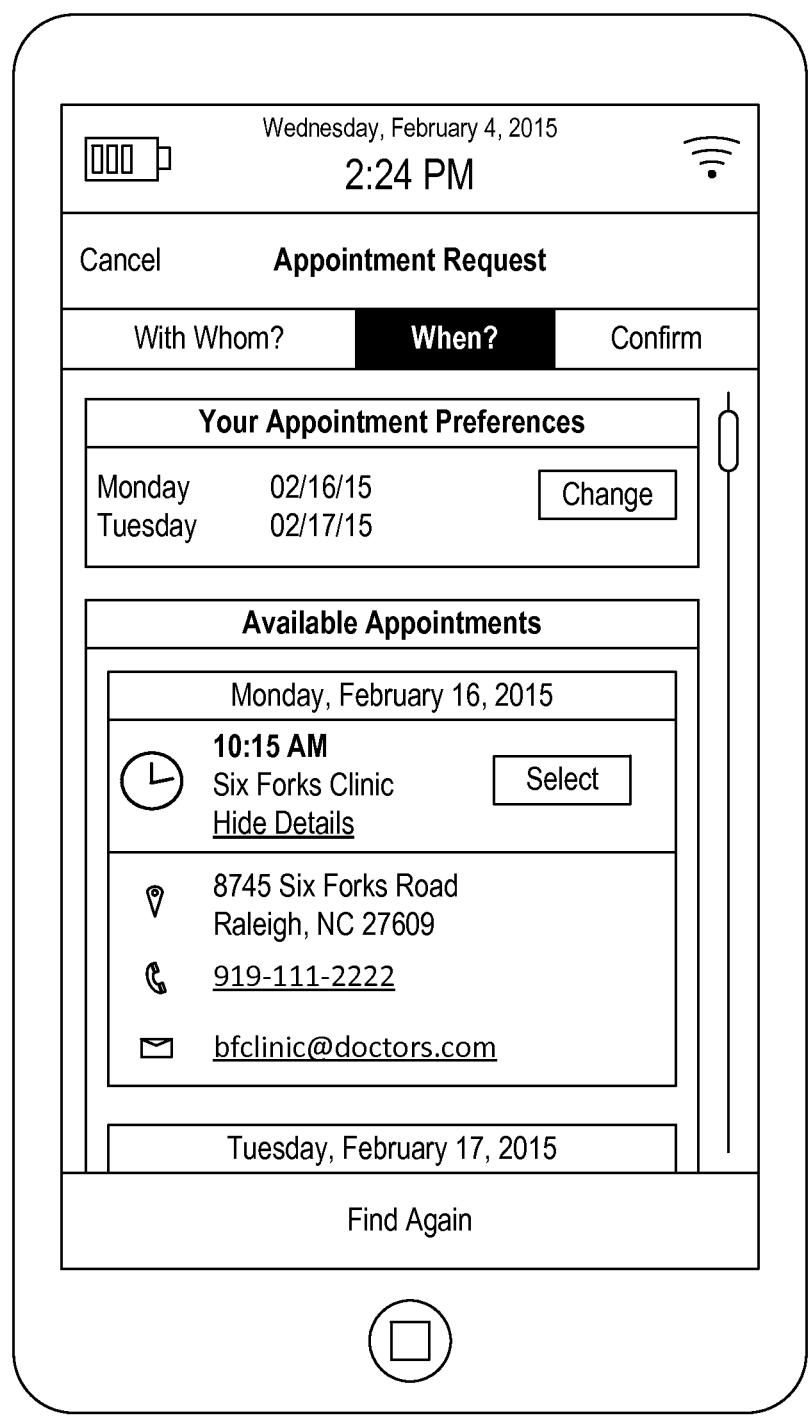
FIG. 15 illustrates the display of additional details for an available appointment time.

FIG. 14 illustrates an exemplary interface indicating availability for selected days. The interface allows a user to select one of the available appointment times, view details for the available appointment times, or go back and try to find another available appointment time. FIG. 15 illustrates the display of additional details for one of the available appointment times.

Figure 16:
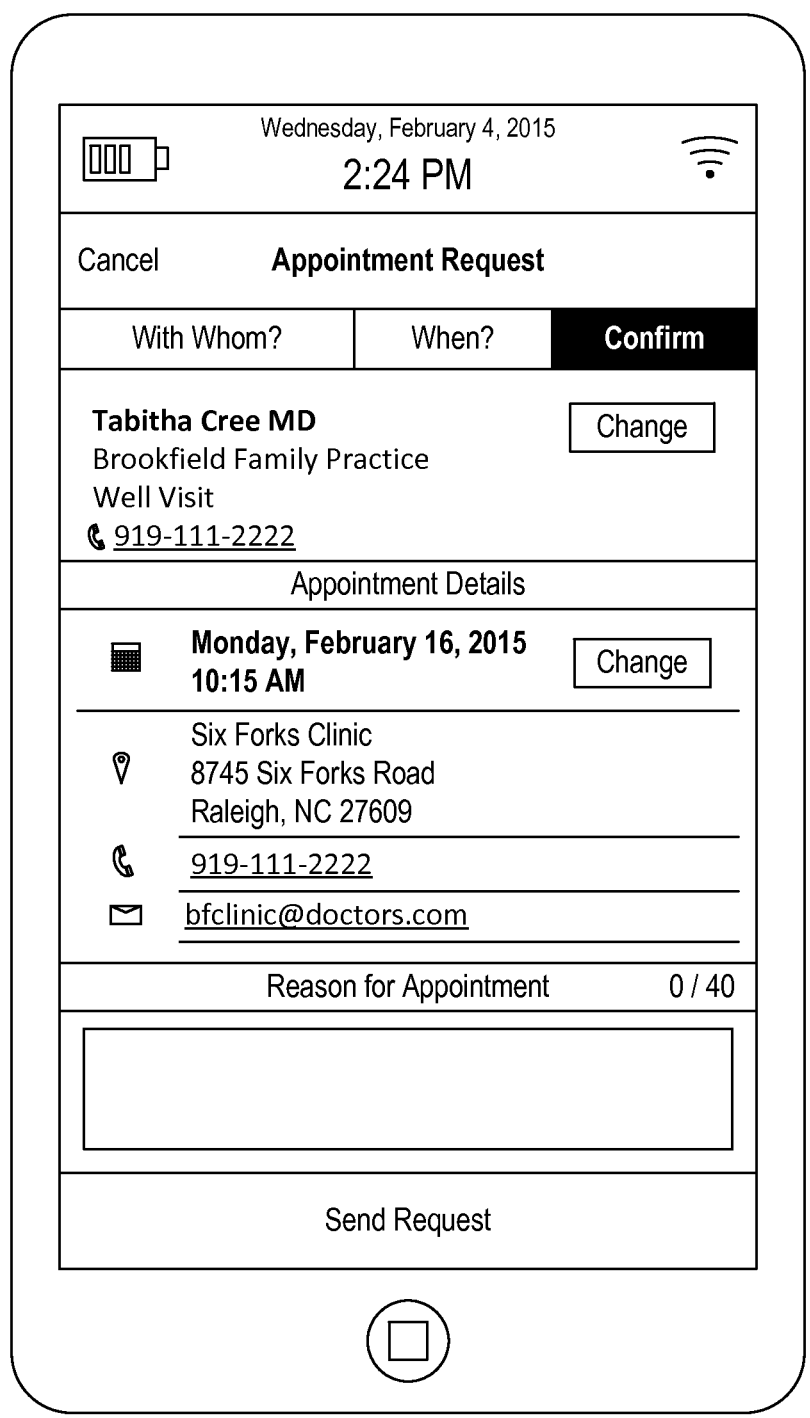
FIGS. 16-17 illustrate a confirmation interface.
Figure 17:
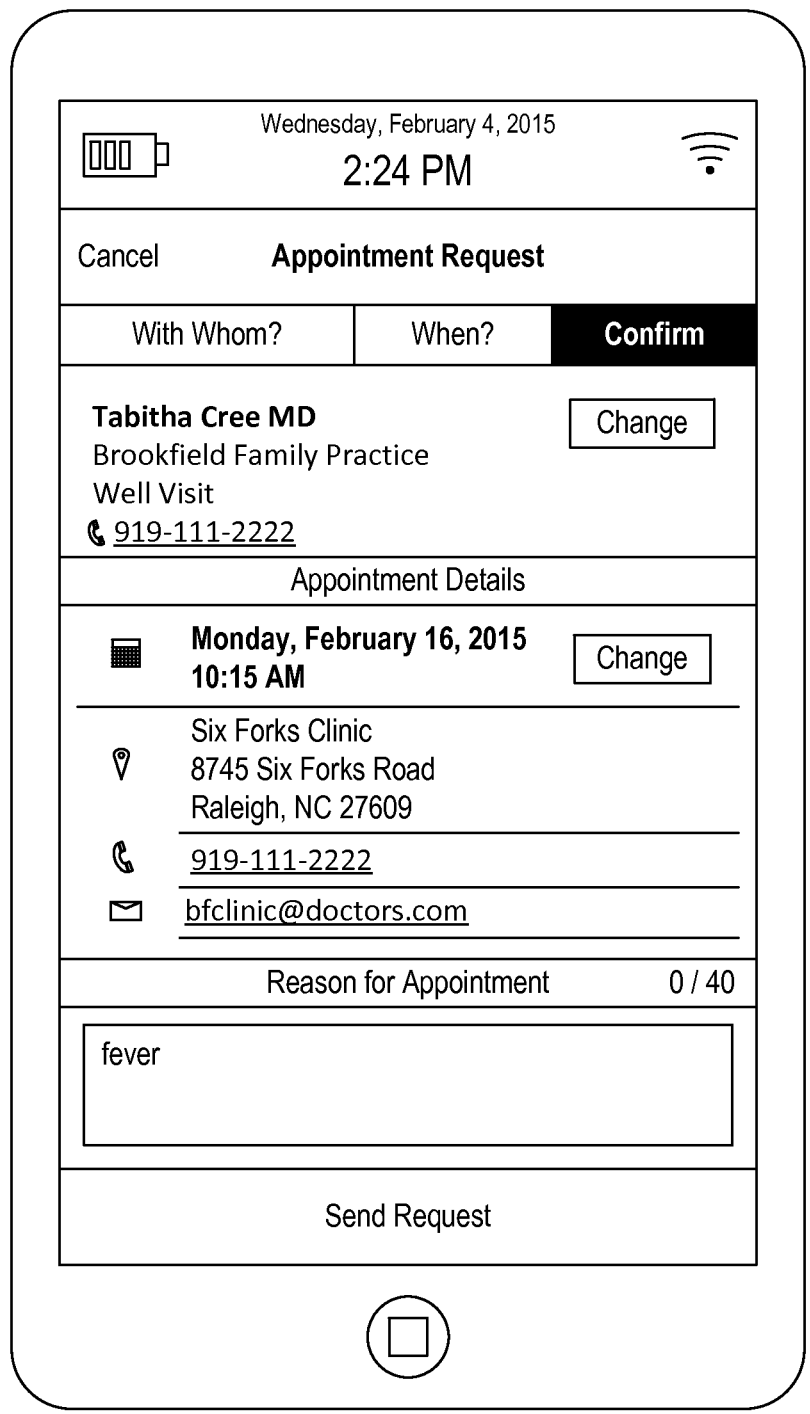

Once a user has located an available appointment date and time that he or she wishes to schedule an appointment at, he or she can select that appointment, which will effect presentation of a confirmation interface, as illustrated in FIG. 16. The confirmation interface will allow a user to input a reason for the appointment, as illustrated in FIG. 17.

Figure 18:
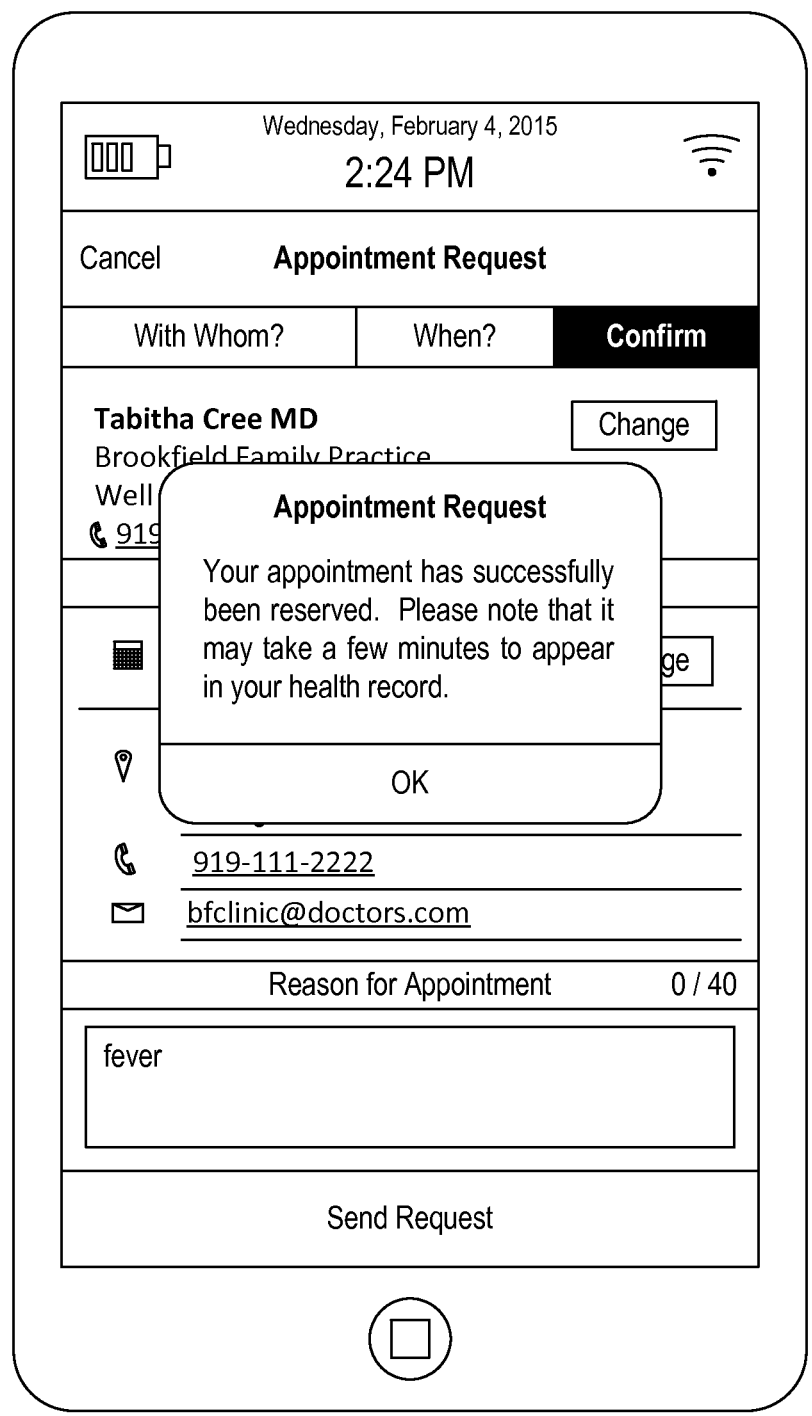
FIG. 18 illustrates an exemplary confirmation message.

Once a user has confirmed and submits an appointment request, the application preferably confirms with the associated practice management system for that provider/organization whether that appointment date and time is in fact still available. If it is, the appointment will be scheduled with the associated practice management system for that provider/organization, and a confirmation will be displayed to the patient user, as illustrated in FIG. 18. The patient will thereafter report to his or her appointment with the healthcare provider at the scheduled date and time.

Figure 19:
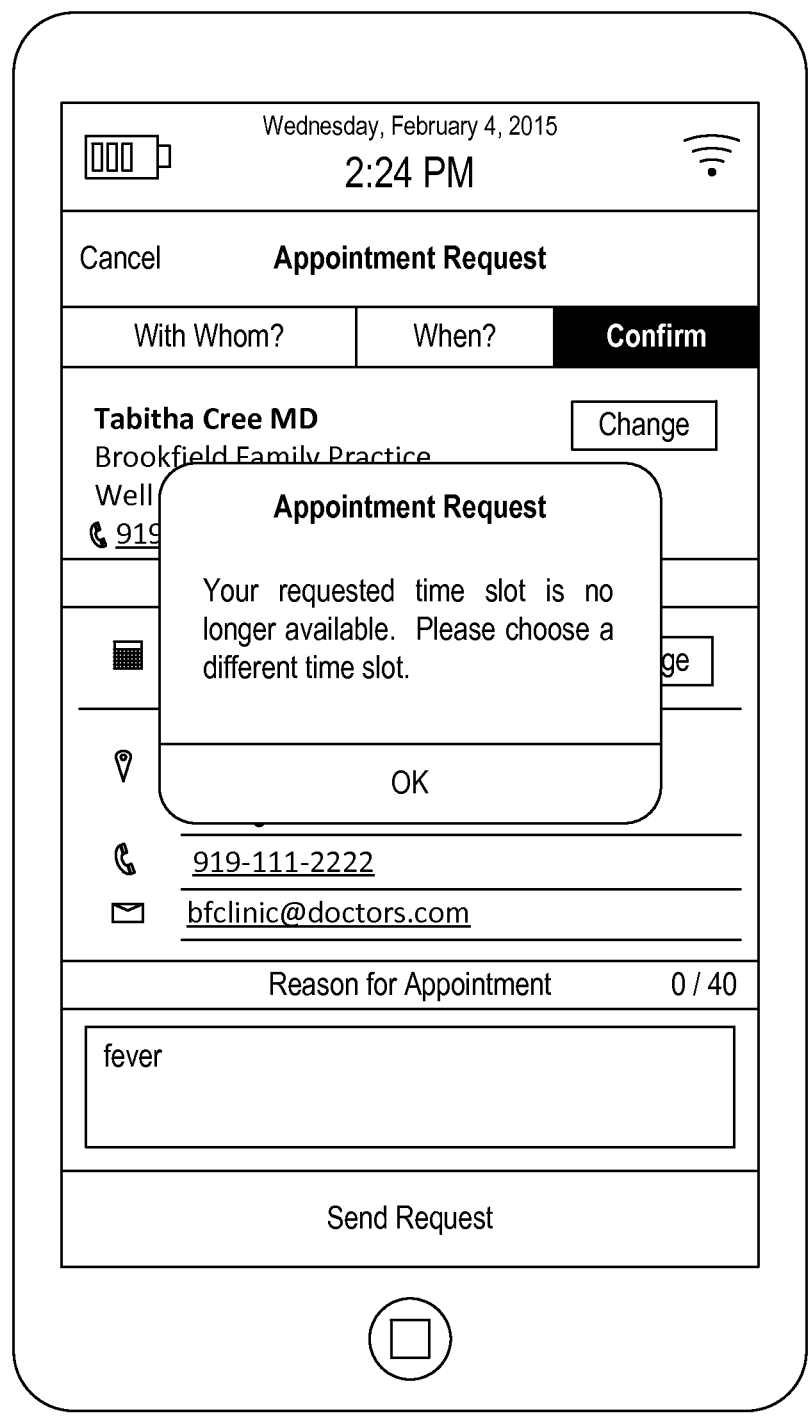
FIG. 19 illustrates an exemplary message window indicating a requested appointment time is no longer available.

If, on the other hand, the requested appointment date and time is for some reason no longer available (e.g. someone else booked it while the user was searching for different dates and times), then the user will be informed of this, as illustrated in FIG. 19.

Figure 20:
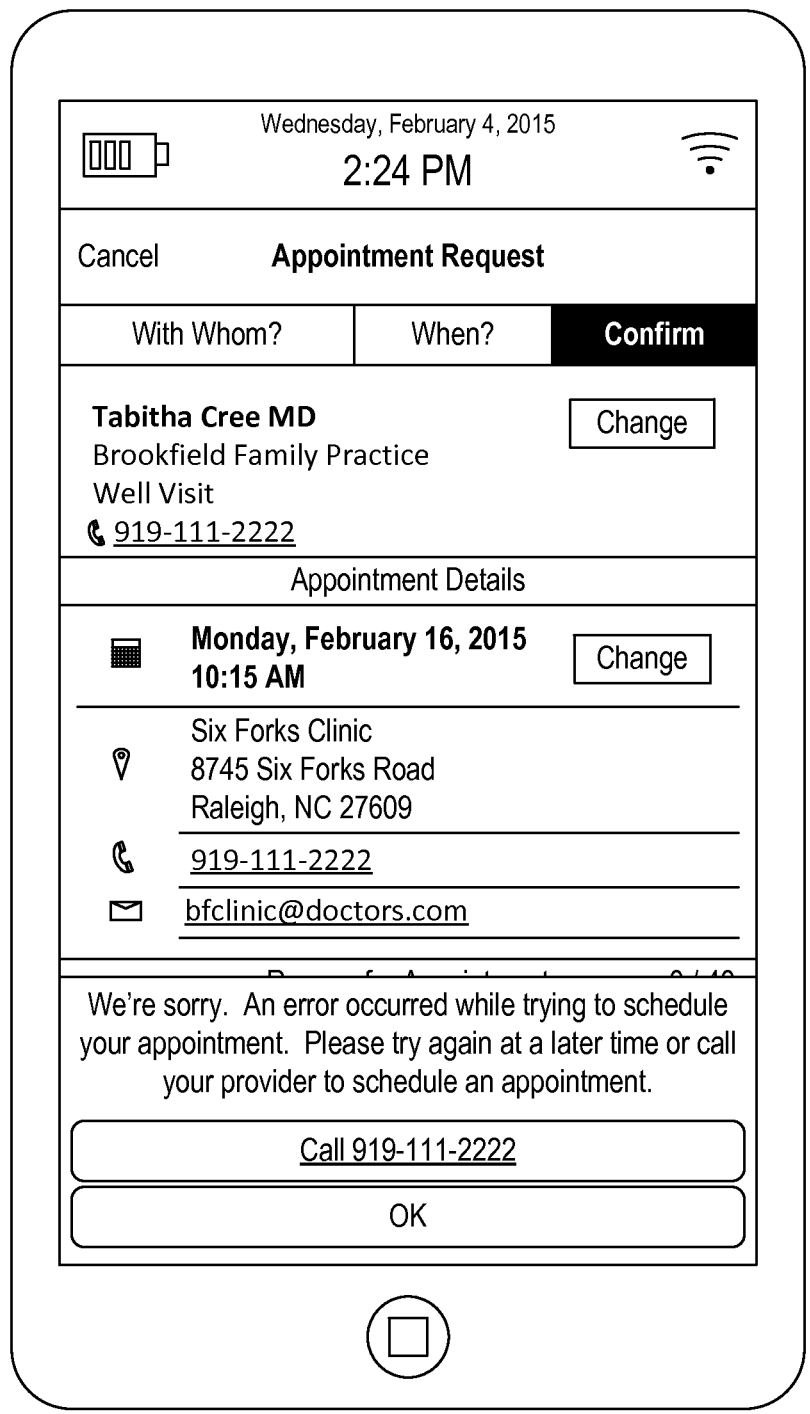
FIG. 20 illustrates an exemplary error message.

In accordance with one or more preferred implementations, if some other type of error occurs (e.g. a network communication failure), a user may be instructed to try again later or call to schedule an appointment, as illustrated in FIG. 20.

Figure 21:
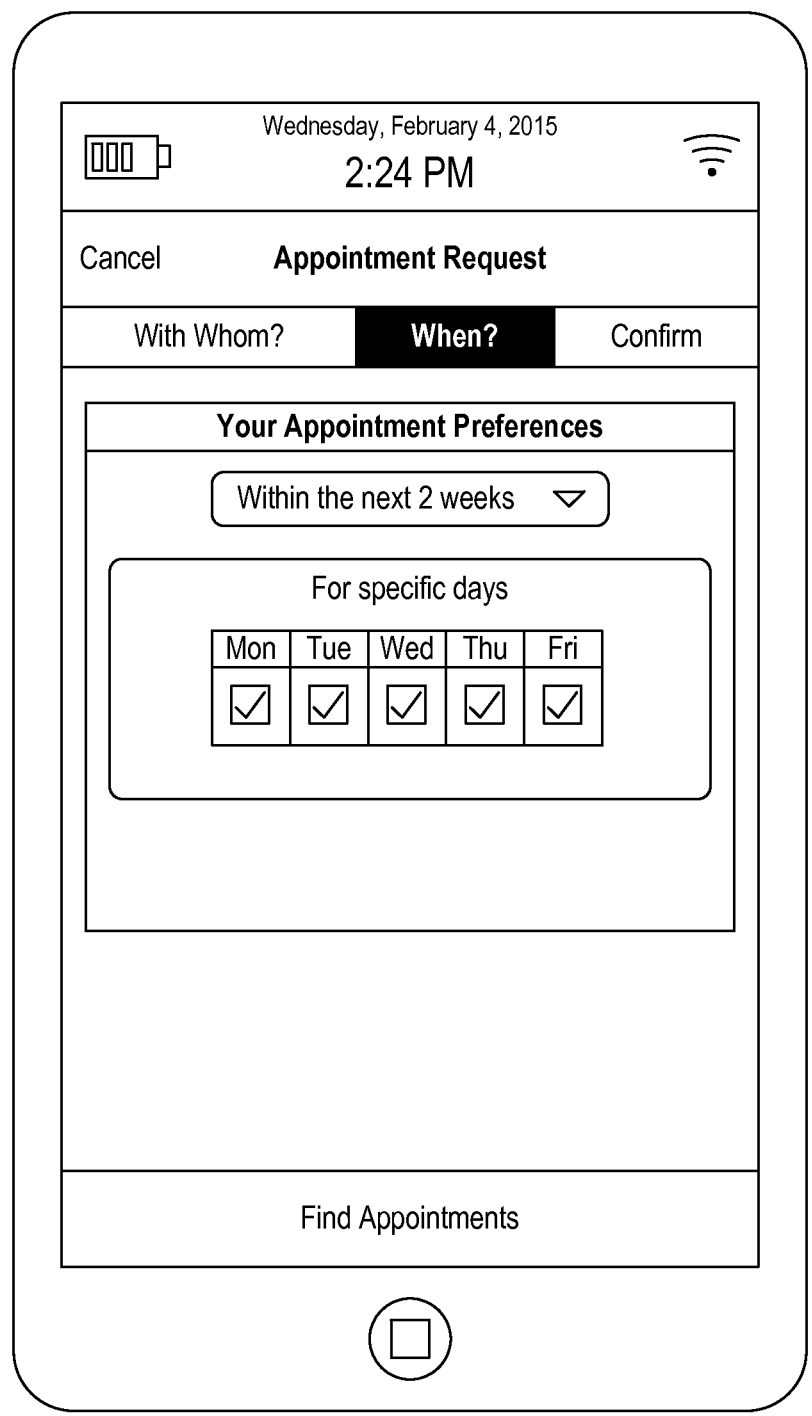
FIG. 21 illustrates an exemplary interface which allows a user to search for available days in a time period.

In accordance with one or more preferred implementations, additionally or alternatively to being able to search for availability on specific dates, a user may be able to search for available days within a time period, e.g. for available Mondays in the next two weeks. FIG. 21 illustrates an exemplary interface which allows a user to search for available days in a time period. In accordance with one or more preferred implementations, this time period defaults to two weeks, but in accordance with one or more preferred implementations, this time period may default to something else. Preferably, upon searching for availability in this manner, a user is presented with an interface displaying available time slots for days within the selected time period. In accordance with one or more preferred implementations, a user may thereafter be presented with, or choose to be presented with, another similar interface for searching over a time period, and/or a date selection interface which allows the user to continue searching.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof

What is claimed is:

1. A method comprising:
   displaying, to a patient via a touchscreen display of a mobile device, an interface of a mobile application which includes a list of providers with whom the patient may schedule an appointment;
   receiving, at the mobile device, first user input on the touchscreen display, the first user input corresponding to selection of a provider in the list of providers;
   displaying, to the patient via the touchscreen display of the mobile device, a date selection interface which includes a calendar display of days in a month;
   (d) receiving, at the mobile device, second user input on the touchscreen display, the second user input corresponding to selection of a day in the month;
   determining, in response to the received second user input corresponding to selection of the day in the month, an available appointment time for the day in the month by querying over a network a practice management system which maintains electronic appointment data for the provider;
   displaying, in response to the received second user input corresponding to selection of the day in the month, an interface on the touchscreen display, wherein the interface displays the determined available appointment time for the day in the month;
   storing, in computer-readable storage of the mobile device, data that indicates that at least one appointment time is available on the day in the month;
   receiving, at the mobile device, third user input on the touchscreen display, the third user input corresponding to an indication to search for a second available appointment time on a different day in the month;
   displaying, on the touchscreen display of the mobile device, an updated date selection interface which has been updated to indicate, based on the data stored in the computer-readable storage that indicates that the at least one appointment time is available on the day in the month, that there is the at least one available appointment time for the day in the month that was previously selected and determined to have the available appointment time;
   receiving, at the mobile device, fourth user input on the touchscreen display, the fourth user input corresponding to selection of a second day in the month;
   determining, in response to the received fourth user input corresponding to selection of the second day in the month, that there are no available appointment times for the second day in the month by querying over the network the practice management system;

displaying, on the touchscreen display and in response to the received fourth user input corresponding to selection of the second day in the month, an interface indicating that there are no available appointment times for the second day in the month;

storing, in the computer-readable storage of the mobile device, second data that indicates that there are no available appointment times for the second day in the month;

receiving, at the mobile device, fifth user input on the touchscreen display, the fifth user input corresponding to an indication to continue searching for the second available appointment time; and displaying, on the touchscreen display of the mobile device and in response to receiving the fifth user input, a second updated date selection interface which has been updated to indicate, based on the data stored in the computer-readable storage that indicates that the at least one appointment time is available on the day in the month, that the at least one available appointment time is available for the day in the month that was previously selected and determined to have the at least one available appointment time, and to indicate, based on the second data stored in the computer-readable storage that indicates that there are no available appointment times for the second day in the month, that there are no available appointment times for the second day in the month that was previously selected and determined to have no available appointment times.

2. The method of claim 1, wherein the mobile device comprises a phone.

3. The method of claim 1, wherein the mobile device comprises a tablet.

4. The method of claim 1, wherein the updated date selection interface comprises a calendar display in which the day in the month is underlined to indicate that the at least one appointment time is available on the day in the month.

5. The method of claim 1, wherein the updated date selection interface comprises a calendar display in which the second day is greyed out to indicate that an appointment time is not available on the second day.

6. A mobile computing device that is configured to perform a plurality of acts, the acts comprising:

displaying, to a patient on a touchscreen display of the mobile computing device, an interface of a mobile application which includes a list of providers with whom the patient may schedule an appointment;

receiving, at the mobile computing device, first user input on the touchscreen display, the first user input corresponding to selection of a provider in the list of providers;

displaying, on the touchscreen display of the mobile computing device, a date selection interface which includes a calendar display of days in a month;

receiving, at the mobile computing device, second user input corresponding to selection of a day in the month, wherein a determination is made by querying over a network a practice management system that maintains electronic appointment data for the selected provider that there are no available appointment times for the day in the month in response to the second user input corresponding to the selection of the first one or more days in the month being received;

displaying, in response to the received second user input corresponding to selection of the day in the month, an interface indicating that there are no available appointment times for the day in the month;

storing, in computer-readable storage of the mobile computing device, first data that indicates that there are no available appointment times for the day in the month;

receiving, at the mobile computing device, third user input on the touchscreen display, the third user input corresponding to an indication to continue searching for available appointment times;

displaying, on the touchscreen display of the mobile computing device, an updated date selection interface which has been updated to indicate, based on the first data stored in the computer-readable storage that indicates that there are no available appointment times for the day in the month, that there are no available appointment times for the day in the month that was previously selected and determined to have no available appointment times;

receiving, at the mobile computing device, fourth user input corresponding to selection of a second day in the month, wherein an available appointment time for the second day in the month is determined by querying over the network the practice management system in response to the received fourth user input corresponding to the selection of the second day in the month;

displaying, in response to the received fourth user input corresponding to selection of the second day in the month, an interface displaying the determined available appointment time for the second day in the month;

storing, in the computer-readable storage of the mobile computing device, second data that indicates that there is at least one available appointment time for the second day in the month;

receiving, at the mobile computing device, fifth user input on the touchscreen display, the fifth user input corresponding to an indication to continue searching for available appointment times; and responsive to receiving the fifth user input on the touchscreen display, displaying, on the touchscreen display of the mobile computing device, a second updated date selection interface which has been updated to indicate, based on the first data stored in the computer-readable storage that indicates that there are no available appointment times for the day in the month, that there are no available appointment times for the day in the month that was previously selected and determined to have no available appointment times, and to indicate, based on the second data stored in the computer-readable storage that indicates that there is the at least one available appointment time for the second day in the month, that there is the at least one available appointment time for the second day in the month that was previously selected and determined to have the at least one available appointment time.

7. The mobile computing device of claim 6 wherein the updated date selection interface comprises a calendar display in which the day in the month is greyed out to indicate that no appointment time is available on the day in the month.

8. The mobile computing device of claim 6 being a mobile phone.

9. The mobile computing device of claim 6, wherein the second updated date selection interface comprises a calendar display in which the day in the month is greyed out to indicate that no appointment time is available on the day in the month.

10. The mobile computing device of claim 6, wherein the second updated date selection interface comprises a calendar display in which the second day in the month is underlined out to indicate that the at least one appointment time is available on the second day in the month.

11. The mobile computing device of claim 6, wherein the second updated date selection interface comprises a calendar display in which the day in the month is greyed out to indicate that no appointment time is available on the day in the month, and the second day in the month is underlined to indicate that the at least one appointment time is available on the second day in the month.

12. A mobile telephone having a touchscreen display, wherein the mobile telephone is configured with instructions that, when executed by a processor of the mobile telephone, are configured to cause the mobile telephone to perform acts comprising:

displaying, to a patient on the touchscreen display of the mobile telephone, an interface of a mobile application which includes a list of providers with whom the patient may schedule an appointment;

receiving, at the mobile telephone, first user input on the touchscreen display, the first user input corresponding to selection of a provider in the list of providers;

displaying, on the touchscreen display of the mobile telephone, a date selection interface which includes a calendar display of days in a month;

receiving, at the mobile telephone, second user input on the touchscreen display, the second user input corresponding to selection of a day in the month, wherein an available appointment time for the day in the month is determined by querying over a network a practice management system which maintains electronic appointment data for the selected provider;

displaying, in response to the received second input corresponding to selection of the day in the month, an interface displaying the determined available appointment time for the day in the month;

receiving, at the mobile telephone, third user input on the touchscreen display, the third user input corresponding to an indication to continue searching for available appointment times;

displaying, on the touchscreen display of the mobile telephone, an updated date selection interface which has been updated to indicate, based on the determination in response to the received second input corresponding to selection of the day in the month, that there is at least one available appointment time for the day in the month that was previously selected and determined to have the at least one available appointment time;

receiving, at the mobile telephone, fourth user input on the touchscreen display, the fourth user input corresponding to selection of a second day in the month, wherein a determination is made by querying over the network the practice management system that there are no available appointment times for the second day in the month in response to the fourth user input corresponding to the selection of the second day in the month being received;

displaying, in response to the received fourth user input corresponding to selection of the second day in the month, an interface indicating that there are no available appointment times for the second day in the month;

receiving, at the mobile telephone, fifth user input, the fifth user input corresponding to an indication to continue searching for available appointment times; and in response to receiving the fifth user input, displaying, on the touchscreen display of the mobile telephone, a second updated date selection interface which has been updated to indicate, based on the determination in response to the received second input corresponding to selection of the day in the month, that there is the at least one available appointment time for the day in the month that was previously selected and determined to have the at least one available appointment time, and to indicate, based on the determination in response to the received fourth user input corresponding to selection of the second day in the month, that there are no available appointment times for the second day in the month that was previously selected and determined to have no available appointment times.

\* \* \* \* \*